(12) United States Patent
Holladay et al.

(10) Patent No.: US 6,743,348 B2
(45) Date of Patent: Jun. 1, 2004

(54) APPARATUS AND METHOD FOR PRODUCING ANTIMICROBIAL SILVER SOLUTION

(76) Inventors: Robert J. Holladay, 490 E. 1200 North, Logan, UT (US) 84341; Herbert Christensen, 816 Cottonwood Cir., Alpine, UT (US) 84004; William D. Moeller, 70 W. Canyon Crest Rd., Suite D, Alpine, UT (US) 84004

( * ) Notice: Subject to any disclaimer, the term of this patent is extended or adjusted under 35 U.S.C. 154(b) by 92 days.

(21) Appl. No.: 09/946,834

(22) Filed: Sep. 4, 2001

(65) Prior Publication Data

US 2002/0071792 A1 Jun. 13, 2002

Related U.S. Application Data

(60) Continuation of application No. 09/716,641, filed on Nov. 20, 2000, now abandoned, which is a division of application No. 09/323,310, filed on Jun. 1, 1999, now Pat. No. 6,214,299.

(51) Int. Cl.[7] .............................. C25C 1/00; C25C 1/20; C25F 7/00
(52) U.S. Cl. ........................ 205/341; 205/571; 205/701
(58) Field of Search ................................ 205/571, 701, 205/341; 204/273, 277, 278, 225

(56) References Cited

U.S. PATENT DOCUMENTS

| | | |
|---|---|---|
| 2,653,893 A | 9/1953 | Romans |
| 3,615,789 A | 10/1971 | Heinrich |
| 3,655,412 A | 4/1972 | Kumai et al. |
| 4,043,932 A | 8/1977 | Fresenius et al. |
| 4,201,635 A * | 5/1980 | Müller .................. 205/339 |
| 5,017,295 A | 5/1991 | Antelman |
| 5,073,382 A | 12/1991 | Antelman |
| 5,078,902 A | 1/1992 | Antelman |
| 5,266,534 A | 11/1993 | Atsumi et al. |
| 5,342,528 A | 8/1994 | Adachi et al. |
| 5,516,519 A | 5/1996 | Oka et al. |
| 5,785,972 A * | 7/1998 | Tyler ..................... 424/195.1 |
| 6,027,469 A * | 2/2000 | Johnson ...................... 604/4 |

OTHER PUBLICATIONS

Ultra Professional Instructions for making premium 'AC' Colloidal Silver with your HVA 'Ultra Professional' System (no date).

* cited by examiner

*Primary Examiner*—Donald R. Valentine
(74) *Attorney, Agent, or Firm*—Clayton, Howarth & Cannon, P.C.

(57) ABSTRACT

An apparatus and method for producing colloidal silver. A large-volume container, such as a fifteen gallon container, includes a hinged lid on which a rotational impeller is mounted along with several sets of electrodes that are electrically connected to a power transformer. The container is partially filled with water, and when the lid is closed, the sets of electrodes are disposed in communication with the water in a predetermined arrangement, and the impeller resides submerged in the water. Certain of the electrodes constitute silver wire. The power transformers convey current to the electrodes, preferably alternating current, at voltages sufficient to cause silver particles to separate from the silver wire and enter the solution in a stable, suspended state. The impeller is rotated, preferably continuously, to prevent the suspended silver from remaining in upper levels of the water, thereby dispersing the silver particles more uniformly throughout the volume of water.

5 Claims, 3 Drawing Sheets

APPARATUS AND METHOD FOR PRODUCING ANTIMICROBIAL SILVER SOLUTION

CROSS-REFERENCE TO RELATED APPLICATIONS

This Application is a con of Ser. No. 09/716,641 Nov. 20, 2000 ABN which IS A div of Ser. No. 09/323,310 Jun. 1, 1999 U.S. Pat. No. 6,214,299

STATEMENT REGARDING FEDERALLY SPONSORED RESEARCH OR DEVELOPMENT

Not Applicable

BACKGROUND OF THE INVENTION

1. The Field of the Invention

The present invention relates generally to colloidal silver, and more particularly, but not exclusively, to a device and method for producing a more stable solution of suspended silver, and in greater batch quantities and at higher rates of production per batch than are presently available.

2. Description of Related Art

It is well known that silver has germicidal properties. In fact, silver was employed as a germicide and antibiotic before modern antibiotics were developed. In previous centuries, users would shave silver particles into their drinking water, or submerge whole silver pieces in the drinking water, for the purpose of ingesting the silver by drinking the water.

Of current interest are apparatus and methods for providing a more effective and stable solution of silver. It is desired to provide colloidal silver to be taken orally for medicinal purposes, as well as to be applied topically and otherwise, for the purpose of enhancing the health of the individual.

There may be many reasons why administering silver suspended in solution would enhance an individual's health. It is possible that such a solution operates to inhibit the growth of bacteria, viruses, and other unwanted organisms, as well as eradicating such existing bacteria, viruses, and other organisms. It is also possible that a solution of silver can have an anti-inflammatory effect, sufficient to reduce symptoms of asthma. Silver in solution might also act in a similar fashion to a homeopathic remedy. These are just a few of the possible reasons why silver in solution, such as colloidal silver, is effective at enhancing health.

Attempts have been made in the prior art to produce silver-based solutions, including colloidal silver, some of which have been more successful than others. Many of the presently available silver-based products, however, are unstable and lose the silver to precipitation. A true colloid operates to maintain the colloidal particles in suspension over a period of several years, and perhaps indefinitely. Many of the silver products fail to maintain the silver particles in suspension, either because the silver solution is not a true colloid or because it is otherwise unstable. When the suspension of the silver particles fails, the particles fall to the bottom of the solution, thereby reducing the solution's concentration of silver and rendering it less effective.

Several U.S. patents describe various ways of making a silver-based solution, including U.S. Pat. No. 2,653,893 (granted Sep. 29, 1953 to Romans), U.S. Pat. No. 5,342,528 (granted Aug. 30, 1994 to Adachi et al., U.S. Pat. No. 4,043,932 (granted Aug. 23, 1977 to Fresenius et al.), U.S. Pat. No. 5,078,902 (granted Jan. 7, 1992 to Antelman), U.S. Pat. No. 5,266,534 (granted Nov. 30, 1993 to Atsumi et al.), U.S. Pat. No. 5,516,519 (granted May 14, 1996 to Oka et al.), U.S. Pat. No. 3,655,412 (granted Apr. 11, 1972 to Kumai et al.), U.S. Pat. No. 3,615,789 (granted Oct. 26, 1971 to Schaller), U.S. Pat. No. 5,785,972 (granted Jul. 28, 1998 to Tyler). Other literature includes "Instructions For Making Premium 'AC' Colloidal Silver," published by CS PRO Systems, Route 7, Box 510GG, San Antonio, Tex. 78264 (date of first publication unknown). These references fail to teach or suggest a process by which stable, colloidal silver may be produced in larger batch quantities and at increased rates of production. Even so, the patents and publications listed above in this paragraph, because of their background relevance, are incorporated herein by reference in their entirety.

The prior art is thus characterized by several disadvantages that are addressed by the present invention. The present invention minimizes, and in some aspects eliminates, the above-mentioned failures, and other problems, by utilizing the methods and structural features described herein.

BRIEF SUMMARY AND OBJECTS OF THE INVENTION

It is therefore an object of the present invention to provide a method and apparatus for producing a silver-based solution.

It is another object of the present invention, in accordance with one aspect thereof, to provide such a method and apparatus for producing colloidal silver.

It is an additional object of the present invention, in accordance with one aspect thereof, to provide such a method and apparatus that is capable of increasing the quantity of silver-based solution produced per batch.

It is a further object of the present invention, in accordance with one aspect thereof, to provide such a method and apparatus that is capable of producing a silver-based solution at a significantly increased rate.

The above objects and others not specifically recited are realized in a specific illustrative embodiment of an apparatus and method for producing colloidal silver. A large-volume container, such as a fifteen gallon container, includes a hinged lid on which a rotational impeller is mounted along with several sets of electrodes that are electrically connected to a power transformer. The container is partially filled with water, and when the lid is closed, the sets of electrodes are disposed in communication with the water in a predetermined arrangement, and the impeller resides submerged in the water. Certain of the electrodes constitute silver wire. The power transformers convey current to the electrodes, preferably alternating current, at voltages sufficient to cause silver particles to separate from the silver wire and enter the solution in a stable, suspended state. The impeller is rotated, preferably continuously, to prevent the suspended silver from remaining in upper levels of the water, thereby dispersing the silver particles more uniformly throughout the volume of water.

Additional objects and advantages of the invention will be set forth in the description which follows, and in part will be apparent from the description, or may be learned by the practice of the invention without undue experimentation. The objects and advantages of the invention may be realized and obtained by means of the instruments and combinations particularly pointed out in the appended claims.

BRIEF DESCRIPTION OF THE DRAWINGS

The above and other objects, features and advantages of the invention will become apparent from a consideration of the subsequent detailed description presented in connection with the accompanying drawings in which.

DETAILED DESCRIPTION OF THE INVENTION

Figure 1:
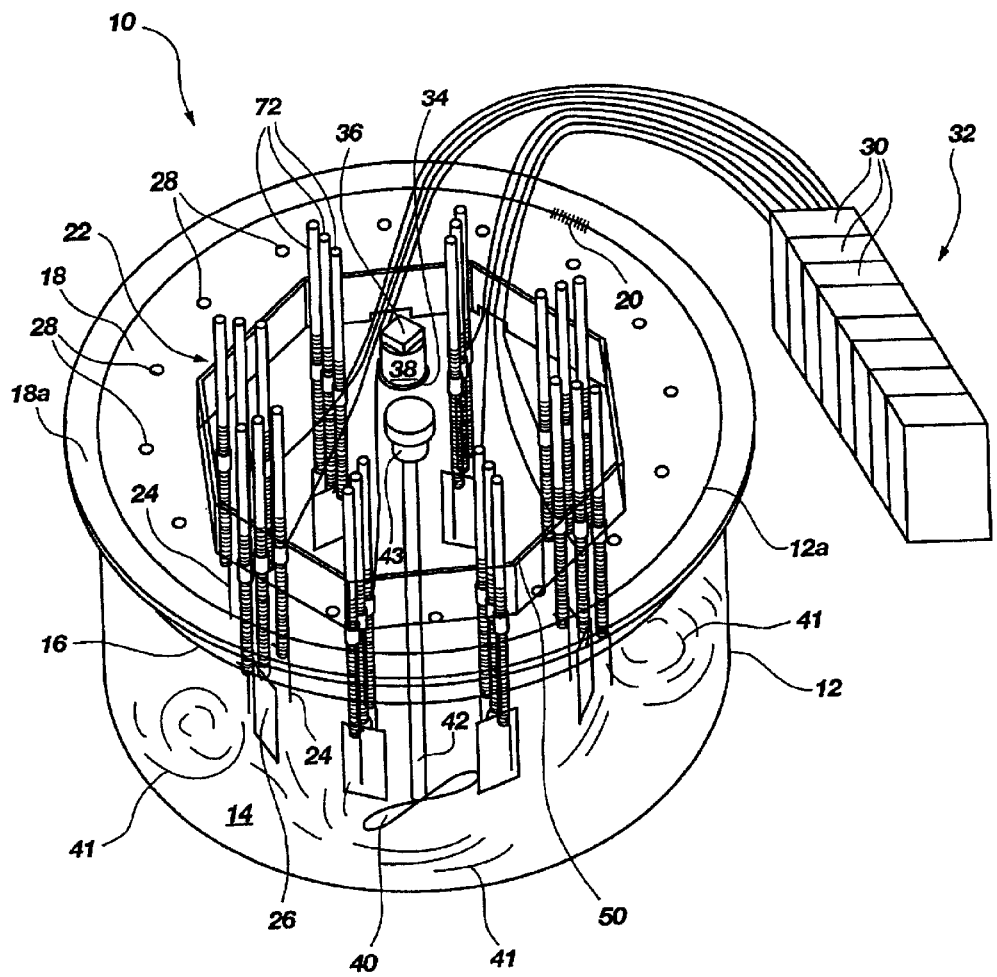
FIG. 1 is a perspective, schematic view of an apparatus for producing colloidal silver, made in accordance with the principles of the present invention.

For the purposes of promoting an understanding of the principles in accordance with the invention, reference will now be made to the embodiments illustrated in the drawings and specific language will be used to describe the same. It will nevertheless be understood that no limitation of the scope of the invention is thereby intended. Any alterations and further modifications of the inventive features illustrated herein, and any additional applications of the principles of the invention as illustrated herein, which would normally occur to one skilled in the relevant art and having possession of this disclosure, are to be considered within the scope of the invention claimed.

Applicants have discovered that the production of a silver-based solution, such as colloidal silver, is greatly enhanced by taking certain measures, such as agitating the solution at a constant, continuous rate during production, and adjusting the height of the silver electrodes during production, as well other steps that are discussed below in more detail.

Figure 2:
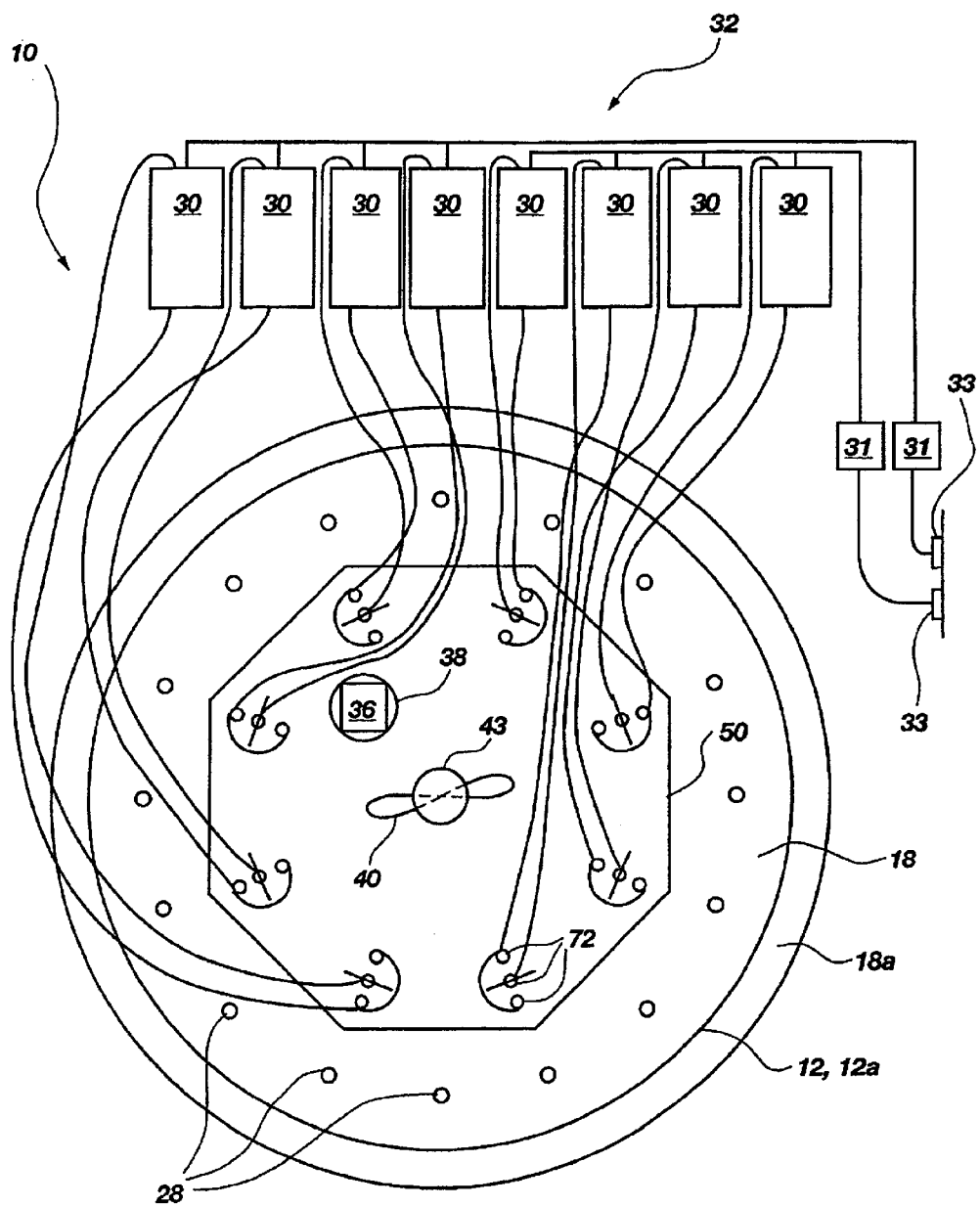
FIG. 2 is a plan view of the apparatus of FIG. 1.

Referring now to FIGS. 1–2, there is shown a apparatus for producing a silver-based solution, the apparatus being designated generally at 10. The apparatus 10 includes a cylindrical, water-tight container 12, for containing a quantity of fluid therein, preferably water 14, said water 14 having an upper surface 16. A lid 18 is provided, preferably connected to the container 12 by a suitable hinge 20.

The apparatus 10 includes several sets 22 of electrodes, eight sets being shown in the embodiment of FIG. 1. Each set 22 preferably includes a pair of upper electrodes 24 connected to each other in parallel, and a lower, center electrode 26. The reference numerals 22, 24 and 26 include lead lines pointing to only one of the eight sets 22 of electrodes for simplicity, but it is to be understood that there are eight sets 22 of electrodes 24 and 26 in FIG. 1.

Each set 22 of electrodes is electrically connected to a power transformer, and each set of electrodes most preferably has its own separate transformer 30. The set of power transformers 30 is referred to as a transformer bank 32. Each transformer 30 produces alternating electrical current at a suitable voltage, presently 10,500 volts, and conveys the current to each pair of upper electrodes 24 in alternating tandem with the center electrode 26, such that the upper electrodes reach a level of +10,500 volts at the same time the center electrode 26 reaches a level of −10,500 volts, and vice versa.

Each set 22 of electrodes is preferably spaced apart from all of the other sets 22 of electrodes by a distance of at least five inches, such that an electrode 24 of one set 22 of electrodes would reside at least five inches away from an electrode 24 of all other sets 22 of electrodes.

The container 12 includes an upper lip 12a upon which the lid 18 rests. The lid 18 is preferably configured and dimensioned to be larger in all lateral directions than the upper lip 12a, such that the lid 18 includes a perimetric overhang 18a extending around the entirety of the upper lip 12a of the container 12. The lid 18 further includes a plurality of air inlet openings 28 formed therein. An air outlet opening 34 is also formed in the lid 18, and an air fan 36 is positioned adjacent to the air outlet opening 34 in a manner such that operation of the fan 36 draws relatively humid air from the container 12 out through the air outlet opening 34 and into atmosphere, thereby causing the surrounding, relatively dryer air to be drawn from atmosphere into the container 12 through the air inlet openings 28. An optional air outlet channel 38 is provided and is attached to the lid 18 to surround the air outlet opening 34, and the air fan 36 is mounted on top of the air outlet channel 38.

An impeller 40 is rotatably attached to the lid by impeller rod 42. The impeller 40 preferably resides in a lower half of the container 12 when the lid 18 is closed upon the upper lip 12a of the container 12. A suitable motor 43 operates the impeller 40 as known to those skilled in the relevant art.

The container 12 and lid 18 are preferably formed from transparent material, such as a plastic having suitable strength. The apparatus 10 further includes a non-conductive housing 50 disposed on top of the lid 18 for covering any live conductive components that feed current to the electrodes 24 and 26, to thereby prevent unsafe human contact with any such conductive components. The non-conductive housing 50 is preferably made from a transparent plastic.

Figure 3:
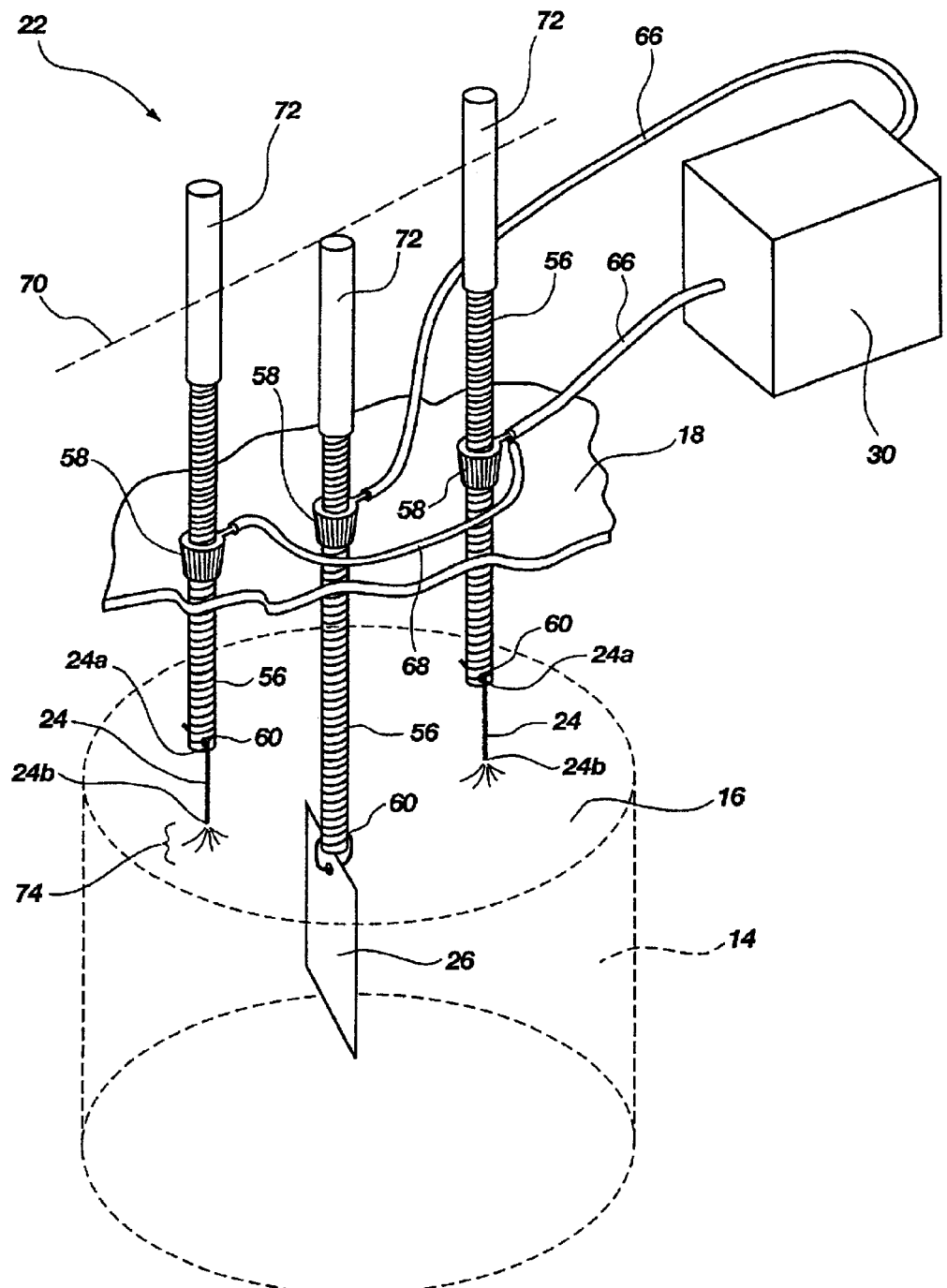
FIG. 3 is a perspective, break-away schematic view of one of the sets of the electrodes of the apparatus of FIG. 1.

Referring now more particularly to FIG. 3, there is shown a perspective, break-away schematic view of one of the sets 22 of electrodes shown in FIG. 1. The pair of upper electrodes 24, and the lower, center electrode 26, are each held in place with a conductive electrode holder 56. The electrode holders 56 are preferably male threaded conductive rods. Conductive, female-threaded mounts 58 are fixedly attached to the lid 18, for mating with the male-threaded holders 56 in threaded engagement. The mounts 58 are electrically connected to the transformer 30 as shown by electrical leads 66. The two outer mounts 58 that correspond to the upper electrodes 24 are electrically connected in parallel by a parallel connector 68. The electrode holders 56 include transverse throughbores 60 formed in distal ends thereof as shown, through which upper ends of the upper electrodes 24 are placed, and through which a conductive connector 62 is placed for connecting the lower, center electrode 26, respectively.

The electrode holders 56 are positioned and arranged such that each holder 56 operates to hold only one electrode 24 or 26. Each set of electrodes corresponds to a set of holders 56, such that each set of holders 56 is spaced apart from all of the other sets of holders 56 by a distance of at least five inches.

The workings of the invention are brought about by forming an electrical circuit with the components described above, in which the circuit would not be closed except for the provision of fluid 14, preferably water having some degree of conductivity to it. The conductivity of the fluid 14 is of course relatively low, making the resistance relatively high at the points where the upper electrodes 24 interface with the fluid 14. The upper electrodes 24 are preferably silver wires, in which case the resistance produced by using the conductive fluid 14 to close the circuit operates to disrupt the silver electrodes 24 and cause particles of silver to separate from the electrodes 24 and enter the fluid 14 in suspension, preferably colloidal suspension. In this manner, as the silver particles are gradually separated from the upper electrodes, the fluid 14 gradually becomes a solution of suspended silver to be taken orally or topically as needed to enhance the personal health of the user. The silver solution fluid 14 may of course be taken or administered in any manner desired.

The positioning of the electrodes 24 and 26 has significance. The inventors have found that production is probably optimized by positioning the upper electrodes 24 such that their distal ends 24b reside above the surface 16 of the fluid 14, and with the lower, center electrode 26 being at least partially submerged within the fluid 14, if not fully submerged. The lower, center electrode 26 is preferably a planar conductive member, thereby providing a large amount of surface area to reduce the concentration of electrical resistance produced by it. The three electrode holders 56 are preferably disposed in a row along a relatively straight line 70, and it is preferable to position the lower, center electrode 70 in a substantially perpendicular orientation with respect to the line 70.

Non-conductive handles 72 are securely attached to upper end of the electrode holders 56 to enable users to turn the electrode holders 56. The handles 72 preferably extend through the housing 50 such that all exposed portions of the electrode holders 56 residing above the lid 18 are contained within the housing 50 to thereby prevent unsafe human contact with such exposed, electrically live portions of the electrode holders 56.

The distal ends 24b of the upper electrodes 24 are preferably maintained above the surface 16 of the fluid 14 at a distance within a range of 0 inches to 1 inch, and more preferably within a range of 0 inches to 3/16 inch. It will be appreciated that the length of the silver-wire upper electrodes 24 becomes gradually reduces as silver particles are disrupted and separated from the distal ends 24b, thereby increasing the distance by which the distal ends 24b reside above the surface 16. When the distal ends 24b are too high above the surface 18, "arcing" occurs, which is accompanied by an electrical arc that is produced between the distal end 24b and the surface 16 of the fluid 14.

Applicants have discovered the colloidal silver produced while arcing occurs for significant periods is at least aesthetically contaminated, and may by contaminated in other ways as well. Suspended silver solution produced by the methods described herein, when utilizing a clear, clean water as the fluid 14, retains a clear, sparkling and desirable appearance when produced without significant periods of arcing. In contrast, when arcing is permitted to occur for significant periods during production of the suspended silver solution, the resulting solution takes on an unpalatable, translucent appearance exhibiting a gray or dark green color.

Applicants have solved the problem of arcing by providing the male-threaded electrode holders 56 disposed in threaded engagement with the female-threaded mounts 58. Users of the apparatus 10 may simply observe the position of the silver-wire upper electrodes 24, and a particular electrode 24 becomes too short, the user can simply twist the corresponding handle 72 in the appropriate rotational direction to cause the electrode holder 56, and hence the corresponding electrode 24, to move closer to the surface 16 of the fluid 14. In this manner, an appropriate distance 74 can be maintained between the distal ends 24b and the surface 16 of the fluid 14, sufficient to prevent arcing from occurring.

It will be appreciated that the apparatus 10 may be operated as described herein to produce colloidal silver. Further, since opinions may differ as to what constitutes a true colloid and what does not, applicants note that the silver-based solution produced by the apparatus 10 has been found to possess all of the several known benefits of silver, including bactericidal benefits and anti-inflammatory benefits. Accordingly, the phrases "silver-based solution," "solution of suspended silver," "silver suspended in solution," and equivalent phrases, as used herein, shall be construed broadly to refer to colloidal silver as well as suspended silver that may not constitute a colloid by some definitions.

It will be appreciated that the container 12 may be referred to as a containing means for containing a quantity of fluid 14 therein such that said fluid 14 includes a free upper surface 16. The upper electrodes 24 may be described as an upper, silver electrode made of silver element and having a first end and a second end.

The electrode holders 56 and the female-threaded mounts 58 may be described collectively as a holding means for (i) holding the first end 24a of the silver upper electrode 24, and (ii) holding the second, distal end 24b of the silver electrode 24 within 0.5 inches of the free upper surface 16 of the fluid 14 when said fluid 14 is contained within the container 12.

The power transformers 30 are controlled by one or more timers 31 as shown in FIG. 2, said timers 31 being electrically connectable to a standard "AC" outlet shown schematically at 33. Each power transformer 30 may be described as a power means electrically connected to the holding means (mounts 58 and electrode holders 56) and to the lower electrode 26 for (i) conveying electrical current through said holding means to the upper, silver electrodes 24 and to said lower electrode 26 in a manner sufficient to produce a voltage difference between said upper and lower electrodes 24 and 26, and (ii) thereby causing particles of silver to separate from the silver electrodes 24 and enter the fluid 14.

The impeller 40 may be referred to as a dispersing means for dispersing the silver particles more evenly throughout the fluid 14 such that a higher quantity of suspended silver particles in solution can be produced per batch. As shown most clearly in FIG. 1, rotational movement of the impeller 40 causes the fluid 14 to flow in internal currents 41 that swirl around the container 12 and cause the dispersing of the silver particles. The impeller 40 may further be described as a means for agitating the fluid 14 at a substantially continuous and substantially constant rate.

Without the agitating, dispersing effect of the impeller 40, the suspended silver particles would tend to remain in an upper layer of the fluid 14. As the silver particles become more concentrated within that upper layer, the conductivity of the fluid in contact with the upper electrodes 24 increases substantially, thereby reducing the electrical resistance, which reduces the rate of production of suspended silver particles. The agitation of the fluid 14 prevents the suspended silver particles from aggregating in the upper level of the fluid 14, and disperses them generally uniformly through the fluid 14, with the result that more suspended silver can be produced per batch, and at a faster rate.

It will be appreciated that any method of agitating the water could be utilized in lieu of the impeller 40 as desired. For example, a circulation pump (not shown) could be utilized in an appropriate manner known to those skilled in the relevant field to cause the fluid 14 to be pumped in a circulating flow, along a flowpath that could either be confined to the container 12 or might alternatively extend beyond the container 12. A further alternative would be to place an air hose into the fluid 14 to dispense air bubbles throughout the fluid 14, thereby agitating the fluid for the benefits described above.

The impeller 40 is preferably disposed in a central location of a horizontal dimension of the container 12. The motor 43 is selected, based upon the viscosity of the fluid 14 and the size of the container 12, to be capable of rotating the impeller 40 at a rotational velocity sufficient to agitate substantially all of any fluid residing in the container 12.

It will be appreciated that the electrode holders 56, with their throughbores 60, constitute a means for holding the first end 24a of the upper, silver electrode 24 in a substantially fixed position in a vertical dimension with respect to said electrode holders 56.

The air fan 36 may be replaced with an air blower, or any other suitable device capable of causing the airflow described herein by operation of the fan 36. The fan 36 may be described as a humidity-reducing means for reducing humidity of air residing within the container 12 above the fluid 14.

In accordance with the features and combinations described above, a preferred method for producing a solution containing silver comprises the steps of:

(a) placing a silver electrode in close proximity to a body of water;

(b) conveying electrical current through the silver electrode to thereby separate particles of silver from said silver electrode in a manner sufficient to cause production of suspended silver particles in solution within the water; and (c) agitating the water during said production of suspended silver particles in solution to thereby disperse the silver particles into a more uniform concentration within said water such that a higher quantity of suspended silver particles in solution can be produced per batch.

An additional and alternative, preferred method for producing a solution containing silver comprises the steps of:

(a) establishing an electrical circuit comprising a current source, and a first conductor electrically connected to said current source and a second conductor electrically connected to said current source, wherein said first conductor resides spaced apart from said second conductor, wherein the first conductor is made of silver element;

(b) closing the circuit by placing the first conductor and the second conductor in communication with a fluidic resistor;

(c) operating the current source to supply alternating current simultaneously to the first conductor and the second conductor such that voltage is increasing and decreasing within the first and second conductors in alternating tandem to thereby cause silver particles to separate from the first electrode and enter the fluidic resistor and become disposed in suspension within said fluidic resistor; and (d) selectively adjusting the first electrode by moving it toward the fluidic resistor as said first electrode decreases in length due to gradual separation of silver particles therefrom to thereby prevent arcing from occurring between said first electrode and said fluidic resistor.

It is to be understood that the above-described arrangements are only illustrative of the application of the principles of the present invention. Numerous modifications and alternative arrangements may be devised by those skilled in the art without departing from the spirit and scope of the present invention and the appended claims are intended to cover such modifications and arrangements. Thus, while the present invention has been shown in the drawings and fully described above with particularity and detail in connection with what is presently deemed to be the most practical and preferred embodiment(s) of the invention, it will be apparent to those of ordinary skill in the art that numerous modifications, including, but not limited to, variations in the processes, size, materials, shape, form, function and manner of operation, assembly and use may be made without departing from the principles and concepts set forth herein.

What is claimed is:

1. A composition of matter comprising:

a therapeutically active compound with anti-bacterial characteristics, said compound comprising a solution of silver particles in suspension at a concentration of at least about 5 ppm, wherein said particles have been removed from a high-resistance end of a silver electrode responsive to alternating current passing through said high-resistance end and said particles being thereafter placed in suspension in a body of flowing liquid.

2. The composition of matter of claim 1, wherein the silver particles have a particle size within a range of about 0.005 micrometers to 0.02 micrometers.

3. A method for producing a solution containing silver, said method comprising the steps of:

(a) placing a silver electrode in close proximity to a body of water;

(b) conveying electrical current through the silver electrode to thereby separate particles of silver from said silver electrode in a manner sufficient to cause production of suspended silver particles in solution within the water; and (c) agitating the water during said production of suspended silver particles in solution to thereby disperse the silver particles into a more uniform concentration within said water such that a higher quantity of suspended silver particles in solution can be produced.

4. A method for producing a solution containing silver, said method comprising the steps of:

(a) establishing an electrical circuit comprising a current source, and a first conductor electrically connected to said current source and a second conductor electrically connected to said current source, wherein said first conductor resides spaced apart from said second conductor, wherein the first conductor is made of silver element;

(b) closing the circuit by placing the first conductor and the second conductor in communication with a fluidic resistor;

(c) operating the current source to supply alternating current simultaneously to the first conductor and the second conductor such that voltage is increasing and decreasing within the first and second conductors in alternating tandem to thereby cause silver particles to separate from the first conductor and enter the fluidic resistor and become disposed in suspension within said fluidic resistor; and (d) selectively adjusting the first conductor by moving it toward the fluidic resistor as said first conductor decreases in length due to gradual separation of silver particles therefrom to thereby prevent arcing from occurring between said first conductor and said fluidic resistor.

5. The method of claim 4, wherein the first conductor and the second conductor form a set of conductors, and wherein the method further comprises the step of:

(e) establishing a plurality of sets of conductors and spacing each set of conductors apart from all of the other sets of conductors by a distance of at least five inches.

* * * * *